(12) United States Patent
Seong (10) Patent No.: US 8,940,531 B2
(45) Date of Patent: Jan. 27, 2015

(54) SYSTEM FOR CULTURING AND RECOVERING MICRO ALGAE

(75) Inventor: Kwang Mo Seong, Gyeonggi-do (KR)

(73) Assignee: Hyundai Motor Company, Seoul (KR)

( * ) Notice: Subject to any disclaimer, the term of this patent is extended or adjusted under 35 U.S.C. 154(b) by 516 days.

(21) Appl. No.: 13/300,893

(22) Filed: Nov. 21, 2011

(65) Prior Publication Data

US 2013/0059368 A1   Mar. 7, 2013

(30) Foreign Application Priority Data

Sep. 2, 2011 (KR) .................. 10-2011-0089245

(51) Int. Cl.
*C12M 1/42* (2006.01)
*C12M 1/00* (2006.01)
*C12N 1/12* (2006.01)
*C12N 1/02* (2006.01)
*C12M 1/26* (2006.01)

(52) U.S. Cl.
CPC .............. *C12M 47/02* (2013.01); *C12M 21/02* (2013.01); *C12M 23/58* (2013.01); *C12M 29/02* (2013.01); *C12M 33/22* (2013.01); *C12N 1/02* (2013.01); *C12N 1/12* (2013.01)
USPC ...................................... 435/292.1

(58) Field of Classification Search
CPC ...... C12M 21/02; C12M 23/58; C12M 29/02; C12M 47/02; C12M 33/22; C12N 1/12; C12N 1/02
See application file for complete search history.

(56) References Cited

U.S. PATENT DOCUMENTS

| 2,083,348 | A | * | 6/1937 | Scholler et al. | ............ 435/295.2 |
| 4,617,113 | A | * | 10/1986 | Christophersen et al. | .... 209/170 |
| 5,944,998 | A | * | 8/1999 | Rolchigo et al. | ............ 210/645 |
| 6,332,980 | B1 | * | 12/2001 | Moorehead | .................. 210/104 |
| 2009/0047722 | A1 | * | 2/2009 | Wilkerson et al. | ......... 435/173.7 |
| 2010/0181234 | A1 | * | 7/2010 | Clayton et al. | ................ 209/164 |

FOREIGN PATENT DOCUMENTS

| JP | 07246086 A | 9/1995 |
| JP | 07289240 A | 11/1995 |
| KR | 10-2005-0081766 | 8/2005 |
| KR | 10-2008-0105008 | 12/2008 |
| KR | 10-2011-0000963 | 1/2011 |
| KR | 10-2011-0029108 | 3/2011 |
| KR | 10-2011-0074768 | 7/2011 |

* cited by examiner

*Primary Examiner* — Nathan Bowers
*Assistant Examiner* — Gautam Prakash
(74) *Attorney, Agent, or Firm* — Edwards Wildman Palmer LLP; Peter F. Corless (57) ABSTRACT

A system for culturing and recovering micro algae comprises a photo-bioreactor, a floatation separator, a centrifugal separator, and a micro bubble generator. The photo-bioreactor unit is configured to culture micro algae by a photochemical reaction to produce a micro algae precipitate. The precipitated micro algae is separated by the floatation separator. The separated micro algae is concentrated by the centrifugal separator. The micro bubble generator generates process water containing micro carbon dioxide bubbles and supplies the generated process water to the photo-bioreactor unit and the floatation separator. With this system, micro algae can be cultured and recovered in a simpler and more cost-effective manner.

9 Claims, 6 Drawing Sheets

SYSTEM FOR CULTURING AND RECOVERING MICRO ALGAE

CROSS-REFERENCE TO RELATED APPLICATION

This application claims under 35 U.S.C. §119(a) the benefit of Korean Patent Application No. 10-2011-0089245 filed Sep. 2, 2011, the entire content of which application is incorporated herein by reference.

BACKGROUND (a) Technical Field

The present invention relates to a system for culturing and recovering micro algae while fixing carbon dioxide.

(b) Background Art

Exhaust gases including carbon dioxide in many fields of industry are required to be treated for environmental consideration. Carbon dioxide can be treated chemically or biologically. One of the biological treatment methods is to use micro algae performing carbon dioxide assimilation. The carbon dioxide treatment using micro algae, however, is slow and requires a large space, which makes it difficult to commercialize the treatment method.

Figure 1:
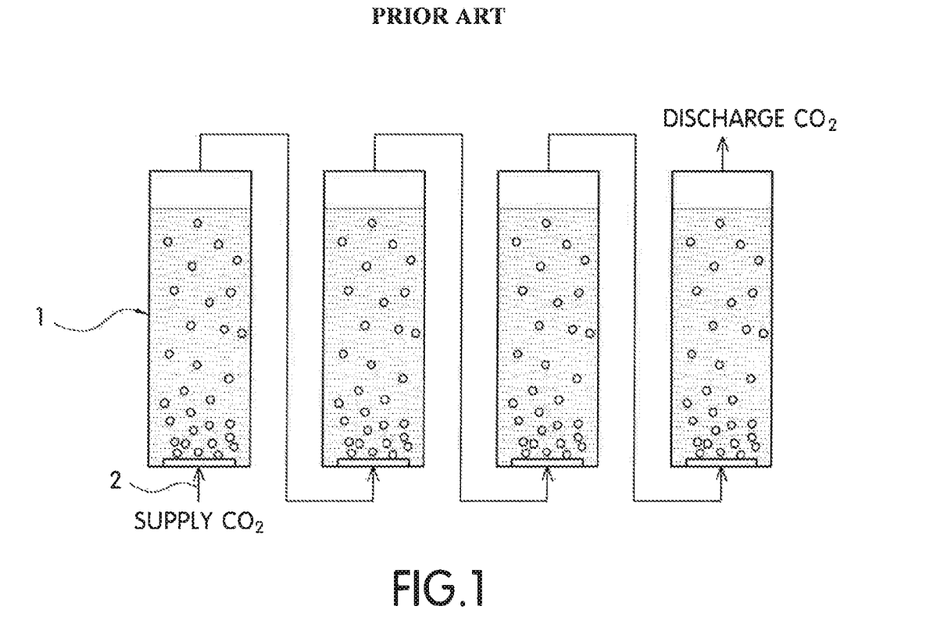
FIG. 1 is a diagram illustrating a conventional system for culturing micro algae using air-lift photo-bioreactors.

FIG. 1 is a diagram illustrating a conventional system for culturing micro algae using air-lift bioreactors. In the conventional system, micro algae are cultured in a culture medium contained in an air-lift photo-bioreactor 1 or air-lift photo-bioreactors 1 installed in series. Carbon dioxide is supplied into the culture medium using a diffuser 2 installed on the bottom of the air-lift photo-bioreactor 1.

Figure 2:
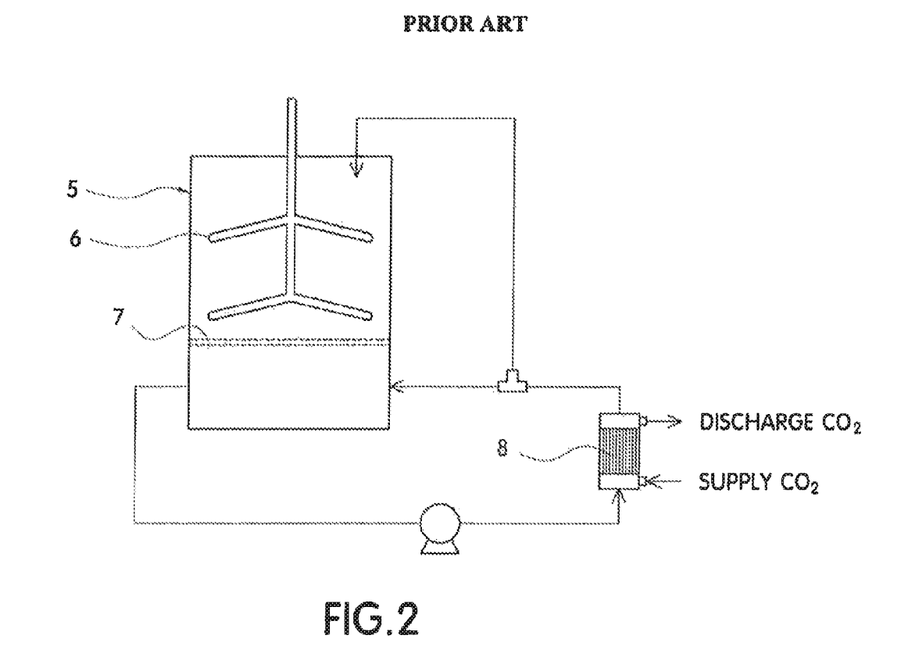
FIG. 2 is a diagram illustrating a conventional system for culturing micro algae using a photo-bioreactor provided therein with a separation membrane.

FIG. 2 is a diagram illustrating a conventional system for culturing micro algae using a photo-bioreactor having therein a separation membrane. Micro algae are cultured in a culture medium contained in a photo-bioreactor 5 provided with a separation membrane 7 and an agitator 6 therein. The culture medium and micro algae are discharged from the photo-bioreactor 5, passed through a hollow fiber membrane 8 with carbon dioxide being introduced, and then introduced to the photo-bioreactor 5.

These conventional systems, however, have problems. For example, the carbon dioxide utilization efficiency is relatively low, precipitated micro algae may cause clogging of a diffuser, a durable separation membrane is relatively expensive, the overall process is quite complicated, and a large space is required for operation of the systems.

The above information disclosed in this Background section is only for enhancement of understanding of the background of the invention and therefore it may contain information that does not form the prior art that is already known in this country to a person of ordinary skill in the art.

SUMMARY OF THE DISCLOSURE

In certain embodiments, a system for culturing and recovering micro algae comprises a photo-bioreactor unit for culturing micro algae by a photochemical reaction to produce a micro algae precipitate, a floatation separator for separating the precipitated micro algae, a centrifugal separator for concentrating the separated micro algae, and a micro bubble generator for generating process water containing micro carbon dioxide bubbles and supplying the generated process water to the photo-bioreactor unit and the floatation separator.

In some embodiments, the system may further comprise a culture medium regenerator for receiving waste culture medium from at least one of the photo-bioreactor unit, the floatation separator, and the centrifugal separator and regenerating the received waste culture medium by supplementing nutrients. Preferably, the regenerated culture medium may be supplied to the photo-bioreactor unit by a circulation pump.

In some embodiments, the photo-bioreactor unit may comprise a photo-bioreactor including: a culture vessel for containing therein culture medium and micro algae; and an overflow pipe longitudinally inserted into the culture vessel such that one end of the overflow pipe is positioned inside culture vessel and the other end of the overflow pipe is positioned outside the culture vessel. In this case, the culture vessel includes an inlet for receiving the regenerated culture medium from the culture medium regenerator, the water containing micro carbon dioxide bubbles from the micro bubble generator, or both, and an outlet for discharging the culture medium, micro algae, or both contained in the culture vessel.

In some embodiments, the photo-bioreactor may be equipped with a micro algae discharger for discharging micro algae precipitated at a lower portion of the culture vessel. The micro algae discharger comprises a hopper for holding therein precipitated micro algae, a precipitation algae transfer pipe connected to a lower end the hopper, and a sensor for measuring the height of the precipitated micro algae in the hopper. The micro algae discharge further comprises an upper separation plate and a lower separation plate. The upper separation plate is provided between the culture vessel and the hopper and configured to be folded such that the culture vessel and the hopper are in communication with each other, if the height of the precipitated micro algae is less than a predetermined value and to be unfolded such that the culture vessel and the hopper are not in communication with each other, if the height of the precipitated micro algae is the same as or greater than the predetermined value. The lower separation plate is provided between the hopper and the precipitation algae transfer pipe and configured to be unfolded such that the hopper and the precipitation algae transfer pipe are not in communication with each other, if the height of the precipitated micro algae is less than the predetermined value and to be folded such that the hopper and the precipitation algae transfer pipe are in communication with each other, if the height of the precipitated micro algae is the same as or greater than the predetermined value. The upper and lower separation plates may, suitably, be driven by a separation plate controller according to a signal from the sensor.

In some embodiments, the floatation separator may comprise a floatation tank for receiving the process water from the micro bubble generator and the micro algae from the precipitation algae transfer pipe and mixing them, a floatation plate disposed in the floatation tank for inducing the micro algae to be floated, a skimmer disposed at an upper portion of the floatation tank for removing the floated micro algae, a micro algae storage tank for storing the micro algae removed by the skimmer, and a waste culture medium storage tank for storing waste culture medium after the removal of micro algae. Preferably, the floatation separator may further comprise a micro bubble floatation plate for inducing micro carbon dioxide bubbles contained in the process water to be floated.

In certain embodiments, the floatation separator may further comprise a micro bubble floatation plate for inducing micro carbon dioxide bubbles contained in the process water to be floated.

In certain embodiments, the micro bubble generator may comprise a supply pump for supplying water to a supply pipe, a storage tank for storing carbon dioxide gas, a supply nozzle for supplying the carbon dioxide gas stored in the storage tank to the supply pipe, and a mixing chamber for receiving and mixing the water and the carbon dioxide gas supplied through the supply pipe to produce the processing water containing micro carbon dioxide bubbles. The mixing chamber may, preferably, comprise an inlet for receiving the water and the carbon dioxide gas supplied through the supply pipe, an outlet for discharging the processing water containing micro carbon dioxide bubbles, and a mixing hose having one end connected to the inlet of the mixing chamber and the other end connected to the outlet of the mixing chamber, and configured to micronize the carbon dioxide gas supplied with the water into micro bubbles to produce the processing water containing micro carbon dioxide bubbles. The mixing chamber may further comprise a support disposed therein around which the mixing hose is spirally wound.

In certain embodiments, the photo-bioreactor unit may comprise a plurality of the photo-bioreactors in series such that culture medium discharged from an outlet of one photo-bioreactor is introduced an inlet of another photo-bioreactor.

The above and other features of the invention are discussed infra.

BRIEF DESCRIPTION OF THE DRAWINGS

The above and other features of the present invention will now be described in detail with reference to certain exemplary embodiments thereof illustrated the accompanying drawings which are given hereinbelow by way of illustration only, and thus are not limitative of the present invention, and wherein.

It should be understood that the appended drawings are not necessarily to scale, presenting a somewhat simplified representation of various preferred features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Hereinafter reference will now be made in detail to various embodiments of the present invention, examples of which are illustrated in the accompanying drawings and described below. While the invention will be described in conjunction with exemplary embodiments, it will be understood that present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

As discussed above, the photo-bioreactor unit may be a single photo-bioreactor or multiple photo-bioreactors installed in series. Hereinafter, the system having multiple photo-bioreactors installed in series, as shown in FIG. 3, will be described for illustration.

Figure 3:
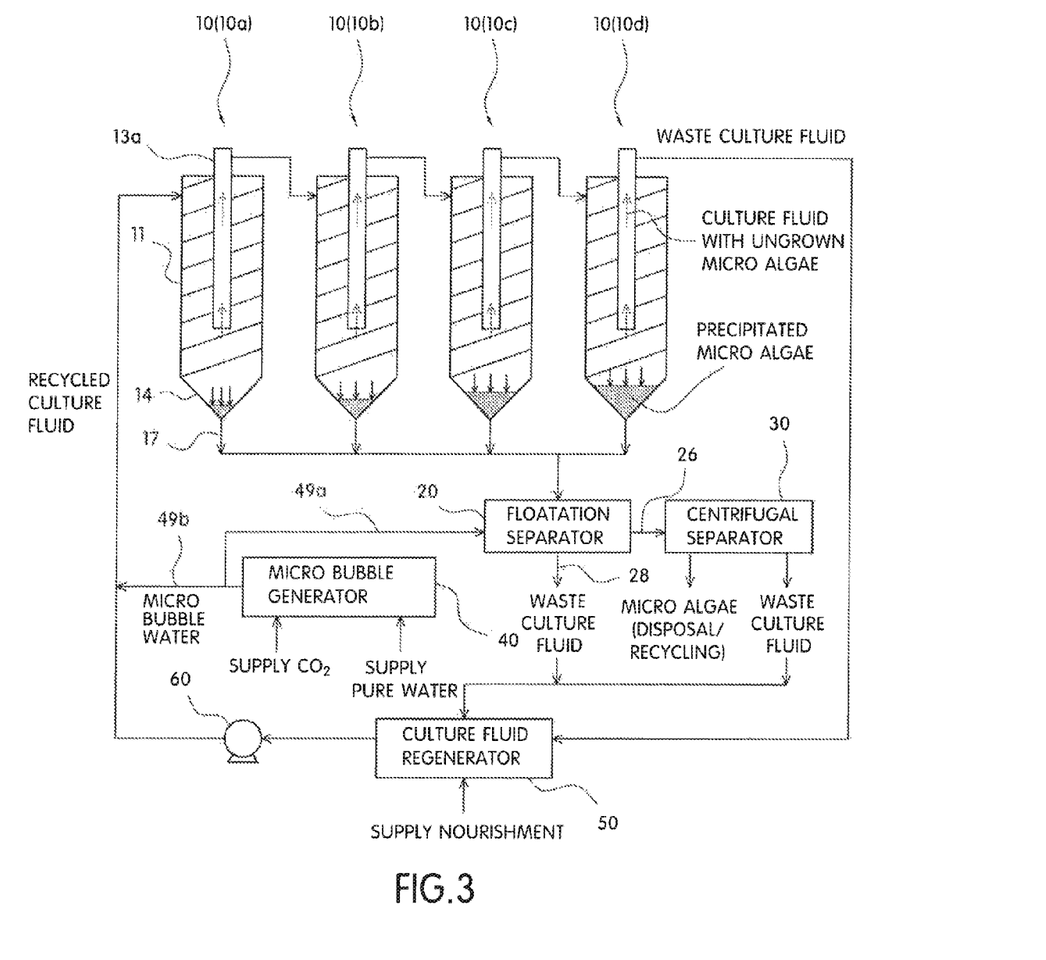
FIG. 3 is a diagram illustrating a system for culturing micro algae using photo-bioreactors according to an embodiment of the present invention.

Referring to FIG. 3, a system for culturing and recovering micro algae, according to an embodiment of the present invention, comprises a photo-bioreactor unit 10 (10a~10d) for culturing micro algae by a photochemical reaction to produce a micro algae precipitate, a floatation separator 20 for separating the precipitated micro algae, a centrifugal separator 30 for concentrating the separated micro algae, and a micro bubble generator 40 for generating process water containing micro carbon dioxide bubbles and supplying the generated process water to the photo-bioreactor unit and the floatation separator. The system may further comprising a culture medium regenerator (50) for receiving waste culture medium from at least one of the photo-bioreactor unit, the floatation separator, and the centrifugal separator and regenerating the received waste culture medium by supplementing nutrients. In this case, the regenerated culture medium may be supplied to the photo-bioreactor unit by, e.g., a circulation pump 60.

Figure 4:
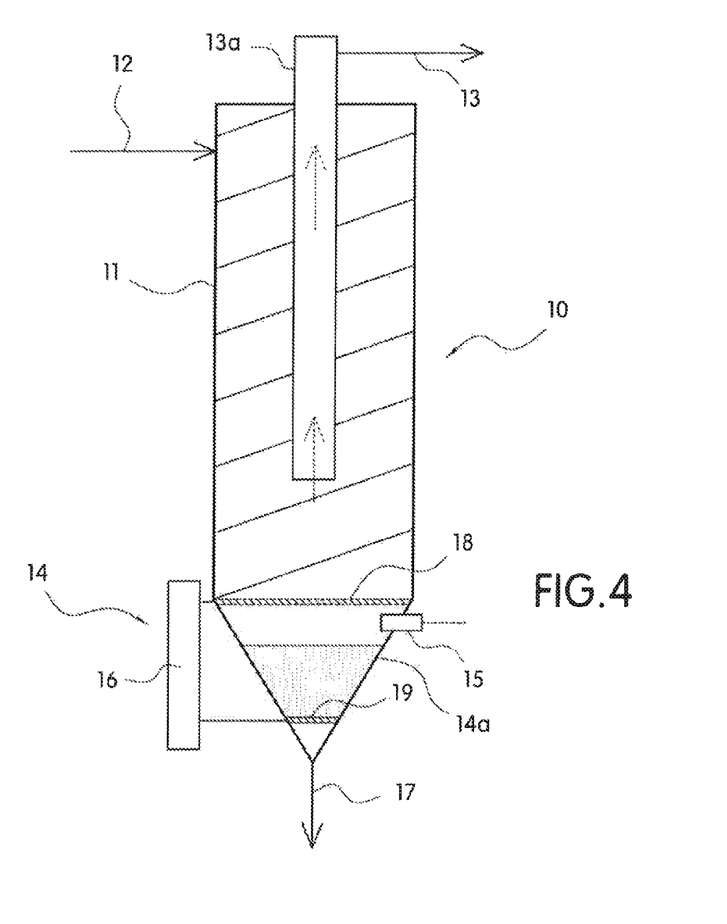
FIG. 4 is a diagram illustrating a photo-bioreactor of the system of FIG. 3.

Referring to FIG. 4, each of the photo-bioreactors 10a, 10b, 10c, 10d may include a culture vessel 11 for containing therein culture medium and micro algae, and an overflow pipe 13a longitudinally inserted into the culture vessel 11 such that one end of the overflow pipe is positioned inside culture vessel 11 and the other end of the overflow pipe is positioned outside the culture vessel 11. The culture vessel 11 includes an inlet 12 for receiving the regenerated culture medium from the culture medium regenerator, the water containing micro carbon dioxide bubbles from the micro bubble generator, or both. The culture vessel also includes an outlet 13 for discharging the culture medium, micro algae, or both contained in the culture vessel.

Preferably, each of the photo-bioreactors 10a, 10b, 10c, 10d is configured to have a cyclonic shape. The photo-bioreactors 10a, 10b, 10c, 10d are disposed in series between the circulation pump 60 and the culture medium regenerator 50 such that the inlet 12 of the photo-bioreactor 10a is connected to the circulation pump 60 and the outlet 13 of the photo-bioreactor 10d is connected to the culture medium regenerator 50. Accordingly, culture medium (with some micro algae) discharged out of the photo-bioreactor 10a may flow into the photo-bioreactor 10b, culture medium (with some micro algae) discharged out of the photo-bioreactor 10b may flow into the photo-bioreactor 10c, and culture medium (with some micro algae) discharged out of the photo-bioreactor 10c may flow into the photo-bioreactor 10d. In this case, culture medium supplied to the inlet 12 of the photo-bioreactor 10a by the circulation pump 60 may be swirled to form a vortex inside the culture vessel 11. Thus, micro algae that have grown over a certain weight may be precipitated on a lower portion of the culture vessel 11 according to the cyclone principle, and remaining micro algae may be discharged to the outlet 13 through the overflow pipe 13a.

Each of the photo-bioreactors is equipped with a micro algae discharger 14 for discharging micro algae precipitated at a lower portion of the culture vessel. Referring to FIG. 4, the micro algae discharger 14 may include a hopper 14a, a sensor 15, an upper separation plate 18, a lower separation plate 19, and a separation plate controller 16. A precipitation algae transfer pipe 17 is connected to a lower end of the hopper 14a.

Micro algae having grown over a certain weight naturally precipitates in the hopper 14a. The sensor 15 measures the height of micro algae precipitated in the hopper 14a. The upper separation plate 18 is provided between the culture vessel 11 and the hopper 14a. The upper separation plate 18 is in a folded state such that the culture vessel 11 and the hopper 14a are in communication with each other, if the height of the precipitated micro algae is less than a predetermined value. The upper separation plate 18 becomes in an unfolded state such that the culture vessel 11 and the hopper 14a are not in communication with each other, if the height of the precipitated micro algae is the same as or greater than the predetermined value. The lower separation plate 19 is provided between the hopper 14a and the precipitation algae transfer pipe 17. The lower separation plate 19 is in an unfolded state such that the hopper 14a and the precipitation algae transfer pipe 17 are not in communication with each other, if the height of the precipitated micro algae is less than the predetermined value. The lower separation plate 19 becomes in a folded state such that the hopper and the precipitation algae transfer pipe are in communication with each other, if the height of the precipitated micro algae is the same as or greater than the predetermined value. That is, when the lower separation plate 19 is folded, the precipitation algae transfer pipe 17 serves to transfer micro algae discharged out of the hopper 14a to the floatation separator 20. The separation plate controller 16 receives a signal from the sensor 15 and driving the upper and lower separation plates 18, 19, respectively.

Figure 5:
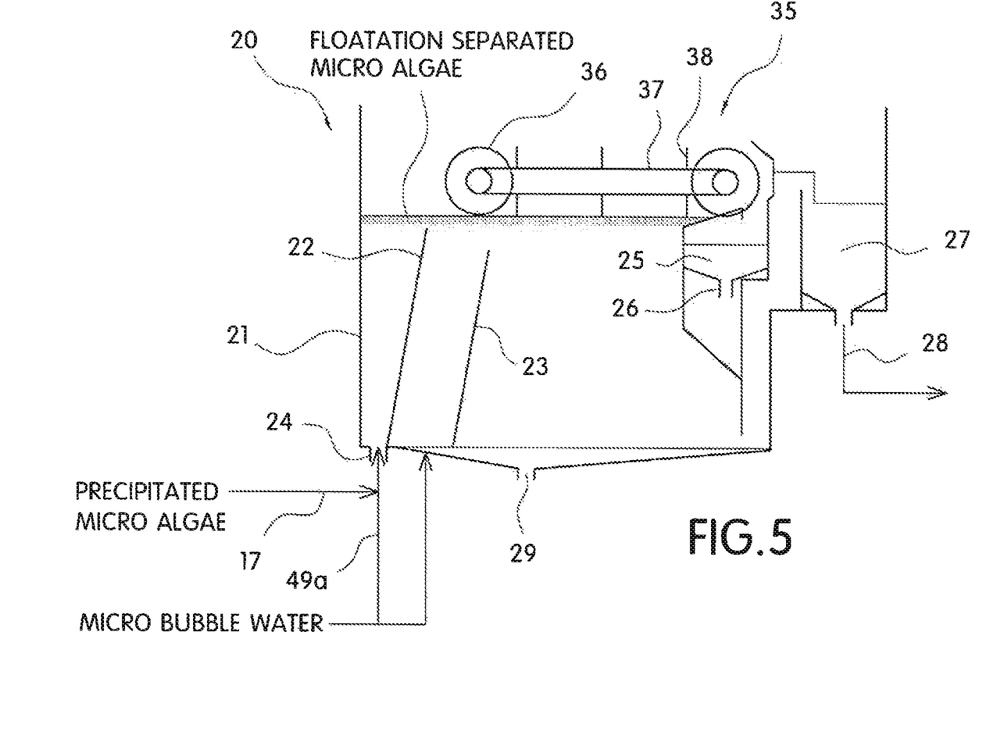
FIG. 5 is a diagram illustrating a floatation separator of the system of FIG. 3

Referring to FIG. 5, the floatation separator 20 may include a floatation tank 21, a floatation plate 22, a skimmer 35, a micro algae storage tank 25, and a waste culture medium storage tank 27. The floatation tank 20 receives the process water from the micro bubble generator 40 and the micro algae from the precipitation algae transfer pipe 17 and mixing them. The floatation plate 22 is disposed in the floatation tank 21 for inducing the micro algae to be floated. The skimmer 35 is disposed at an upper portion of the floatation tank 21 for removing the floated micro algae. The micro algae storage tank 25 stores the micro algae removed by the skimmer 35. The waste culture medium storage tank 27 stores waste culture medium after the removal of micro algae. A micro bubble water transfer pipe 49a may be connected between the floatation tank 21 and the micro bubble generator 40. The precipitation algae transfer pipe 17 may be connected between the floatation tank 21 and the photo-bioreactors 10.

As shown in FIG. 5, the micro bubble water transfer pipe 49a and the precipitation algae transfer pipe 17 may be introduced into the floatation tank 21 through an inlet 24 disposed at a lower portion of the floatation tank 21 for smooth mixture of micro algae and micro bubble water introduced into the floatation tank 21. The floatation plate 22 may be disposed at the side of the inlet 24 of the floatation tank 21 to induce the floatation of micro algae stuck with micro bubbles.

Micro algae and micro bubble water introduced into the floatation tank 21 may be mixed while being introduced into a gap between the floatation plate 22 and the floatation tank 21. In this case, micro algae stuck with micro bubbles may rise to the upper portion of the floatation tank 21 along the floatation plate 22.

In order to increase the floatation separation efficiency of micro algae, a micro bubble floatation plate 23 may be disposed near the floatation plate 22 (e.g., at the rear of the floatation plate 22) to induce the floatation of micro bubbles in micro bubble water that is additionally supplied into the floatation tank 21 without being mixed with micro algae. Preferably, the floatation plate 22 and the micro bubble floatation plate 23 may be obliquely disposed to increase the floatation efficiency.

An outlet 29 for discharging all contents of the floatation tank 21 may be disposed at a lower end of the floatation tank 21 in which the floatation separation is performed. The outlet 29 may be opened during repair and cleaning of the floatation separator 20 to discharge all contents of the floatation tank 21.

The skimmer 35 may be disposed at an upper end of the floatation tank 21 to collect and remove micro algae that float on the floatation tank 21. The skimmer 35 may include a pair of support rollers 36, a drive chain 37, and a scraper 38. The pair of support rollers 36 may be driven by a drive motor (not shown). The drive chain 37 may be connected between the pair of support rollers 36, and may rotate in linkage with the rotating operation of the support roller 36. The scraper 38 may be integrally formed on the drive chain 37 to collect micro algae floating on the floatation tank 21 and transfer micro algae to the micro algae storage tank 25.

The micro algae storage tank 25 may be disposed at an appropriate place (e.g., opposite side of the floatation plate) where (floatation separated) micro algae transferred by the scraper 38 can be stored at one side of the floatation tank 21. A floatation algae transfer pipe 26 may be connected to the lower end of the micro algae storage tank 25 to transfer micro algae that are stored to the centrifugal separator 30.

The waste culture medium storage tank 27 may be disposed at the opposite side of the floatation plate 22 and may store waste culture medium from which micro algae are removed. Since micro algae are naturally precipitated by the weight thereof, the waste culture medium storage tank 27 disposed at an upper portion of the opposite side of the floatation plate 22 and the micro bubble floatation plate 23 and installed at the rear of the micro algae storage tank 25 may receive waste culture medium as the water level of waste culture medium at the upper portion of the floatation tank 21 becomes higher than the storage tank 27. In this case, micro algae that are floated and separated at the upper portion of the floatation tank 21 may be interrupted and separated by the storage tank 25 so as not to flow into the storage tank 27, allowing only waste culture medium to flow into the storage tank 27.

The waste culture medium transfer pipe 28 may be connected to the lower end of the storage tank 27 to transfer waste culture medium that is stored to the culture medium regenerator 50.

The centrifugal separator 30 may be configured with a typical centrifugal separator. Micro algae that are recovered and concentrated by the centrifugal separator 30 may be disposed of or recycled into materials for biodegradable plastic or biofuel. Waste culture medium that is separated and recovered from micro algae may be transferred to the culture medium regenerator 50 to be regenerated or recycled.

Figure 6:
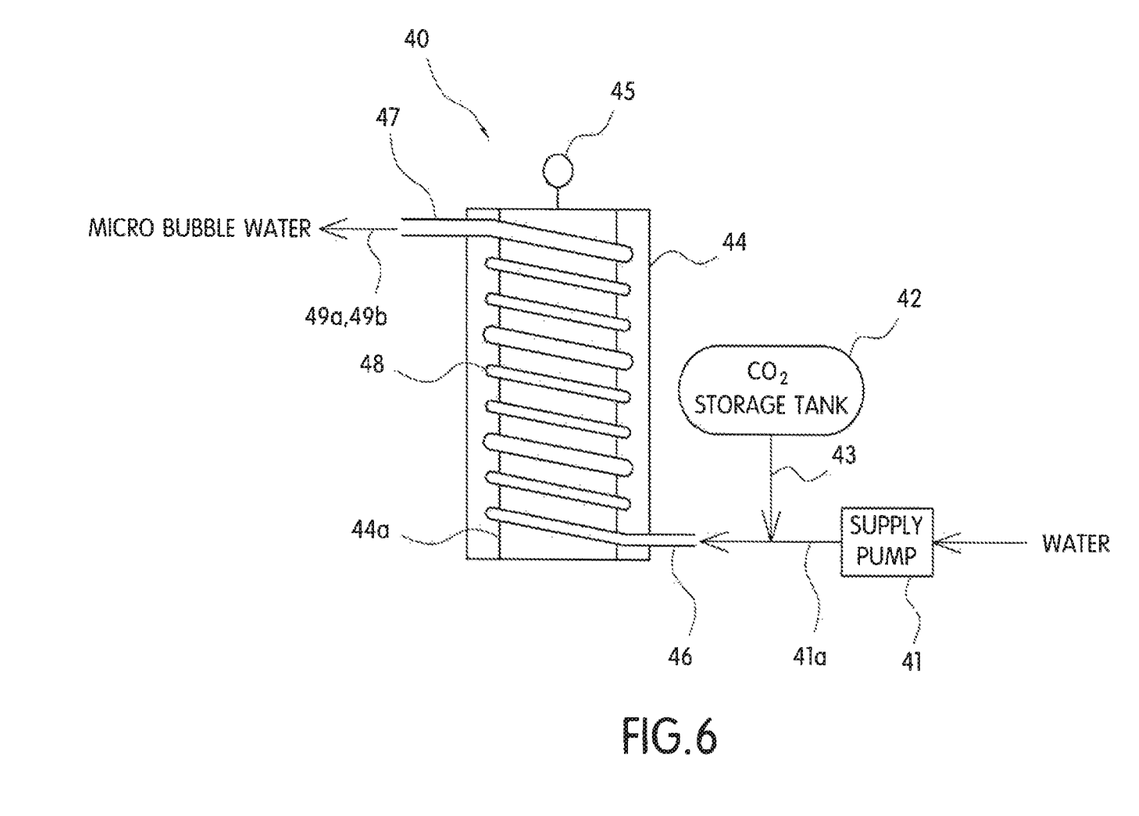
FIG. 6 is a diagram illustrating a micro bubble generator of the system of FIG. 3.

As shown in FIG. 6, the micro bubble generator 40 may include a supply pump 41, a $CO_2$ storage tank 42, a $CO_2$ supply nozzle 43, and a mixing chamber 44. The supply pump 41 supplies water to a supply pipe 41a connected between the supply pump 41 and the mixing chamber 44. The storage tank 42 stores carbon dioxide gas. The supply nozzle 43 supplies the carbon dioxide gas stored in the storage tank to the supply pipe 41a. The mixing chamber 44 receives and mixes the water and the carbon dioxide gas supplied through the supply pipe 41a to produce the processing water containing micro carbon dioxide bubbles. The mixing chamber 44 has an inlet 46 or receiving the water and the carbon dioxide gas supplied through the supply pipe and an outlet 47 for discharging the processing water containing micro carbon dioxide bubbles.

Referring to FIG. 6, the mixing chamber may include a cylindrical support 44a therein, which may occupy most internal space of the mixing chamber 44. A mixing hose 48 may be spirally wound around the support 44a. The mixing hose 48 may have both ends connected to the inlet 46 and the outlet 47, respectively. The mixing hose 48 may be configured such that a hose of a relatively smaller diameter and a hose of a relatively greater diameter are alternately connected to each other. In other words, the diameter of the mixing hose 48 may vary at every certain interval. Accordingly, since the flow speed of water saturated with $CO_2$ gas may vary while water is passing through the mixing hose 48, micro bubbles may be generated in water.

Also, a filter member (not shown) having a fine hole of a micrometer size may be disposed at the end portion (at the side of micro bubble water outlet) to split $CO_2$ bubbles contained in water into micrometer sizes (e.g., about 30 μm)

Furthermore, a pressure gauge 45 may be disposed on the mixing chamber 44 to display the internal pressure of the mixing hose 48, and micro bubble water transfer pipes 49a and 49b may be disposed to transfer generated micro bubble water to the photo-bioreactor unit 10 and the floatation separator 20.

The culture medium regenerator 50 may receive waste culture medium generated in the photo-bioreactors 10, the floatation separator 20, and the centrifugal separator 30, and may supply and mix waste culture medium with nutrients necessary for the growth of micro algae to regenerate the waste culture medium.

The culture medium regenerated in the culture medium regenerator 50 may be supplied to the photo-bioreactors 10 through the circulation pump 60. In this case, the culture medium may be mixed with micro bubble water supplied through the micro bubble water transfer pipe, and then may be supplied to the photo-bioreactors 10.

Hereinafter, an operation of the system according to an embodiment of the present invention will be described in detail.

A certain amount of culture medium is filled in the photo-bioreactor unit 10, and then micro algae may be inoculated into the culture medium. Thereafter, visible light (sunlight, artificial light, and a combination thereof) is irradiated.

Culture medium is supplied into the culture vessel 11 of the first photo-bioreactor 10 by the circulation pump 60, creating a vortex. According to the cyclone principle, micro algae having grown over a certain weight are precipitated on a lower portion of the photo-bioreactor 10a, and remaining micro algae are discharged together with culture medium to be transferred to the second photo-bioreactor 10b connected to the first photo-bioreactor 10a.

In the second photo-bioreactor 10b, the culture medium and micro algae are mixed by a vortex generated due to the culture medium introduced from the first photo-bioreactor 10a. According to the cyclone principle, micro algae having grown over a certain weight are precipitated on a lower portion of the photo-bioreactor 10b, and remaining micro algae are discharged together with culture medium to be transferred to the third photo-bioreactor 10c connected to the second photo-bioreactor 10b.

In the third photo-bioreactor 10c, the culture medium and micro algae are mixed by a vortex generated due to the culture medium introduced from the second photo-bioreactor 10b. According to the cyclone principle, micro algae having grown over a certain weight are precipitated on a lower portion of the photo-bioreactor 10c, and remaining micro algae are discharged together with culture medium to be transferred to the fourth photo-bioreactor 10d connected to the third photo-bioreactor 10c.

In the fourth photo-bioreactor 10d, the culture medium and micro algae are mixed by a vortex generated due to the culture medium introduced from the third photo-bioreactor 10c. According to the cyclone principle, micro algae having grown over a certain weight are precipitated on a lower portion of the photo-bioreactor 10d, and remaining micro algae are discharged together with culture medium to be transferred to the culture medium regenerator 50 connected to the fourth photo-bioreactor 10d.

In this case, micro algae precipitated in each photo-bioreactor 10 are deposited in the hopper 14a of the micro algae discharger 14. When precipitated micro algae are deposited at a predetermined height in the hopper 14a, the upper and lower separation plates 18 and 19 are driven by a signal of the sensor 15 to allow micro algae deposited in the hopper 14a to be discharged into the precipitation algae transfer pipe 17. That is, the upper separation plate 18 becomes unfolded and the lower separation plate 19 becomes folded thereby allowing micro algae deposited in the hopper 14a to go down to the precipitation algae transfer pipe 17. Micro algae discharged into the precipitation algae transfer pipe 17 are supplied to the floatation separator 20.

When discharge of all micro algae deposited in the hopper 14a is completed, the micro algae discharger 14 may be again driven to allow the lower separation plate 19 to be unfolded and upper separation plate 18 to be folded by the separation plate controller 16, thereby allowing micro algae to be precipitated in the hopper 14a.

As described above, micro algae precipitated in and discharged from the photo-bioreactors 10 are then transferred to the floatation separator 20. The floatation separator 20 floatation-separates the introduced micro algae using the floatation plate 22 and the $CO_2$ bubbles of micro bubble water supplied from the micro bubble generator 40.

Micro algae that have been floatation separated are collected and removed by the skimmer 35, and transferred to the micro algae storage tank 25 to be concentrated and stored therein. Thus, concentrated micro algae are transferred to the centrifugal separator 30 through the floatation algae transfer pipe 26.

Waste culture medium generated during the floatation-separation and concentration processes of micro algae may be stored in the storage tank 27, and then transferred to the culture medium regenerator 50 through the waste culture medium transfer pipe 28.

Micro algae transferred through the floatation algae transfer pipe 26 may be separated and recovered by the centrifugal separator 30 to be further concentrated, and recovered micro algae may be disposed of or recycled into materials for biodegradable plastic or biofuel. Waste culture medium generated during the recovery process of micro algae using a centrifugal force may be transferred to the culture medium regenerator 50.

Culture medium regenerated by supplying nutrients in the culture medium regenerator 50 may be transferred to the first photo-bioreactor 10a by the circulation pump 60.

On the other hand, in the processes for generating and supplying micro bubble water, $CO_2$ micro bubbles may be generated using Bernoulli's principle "in a steady flow, the sum of all forms of mechanical energy in a fluid along a streamline is the same at all points on that streamline".

Specifically, water for generating micro bubbles may be supplied to the mixing hose 48 of the mixing chamber 44 via the water supply pipe 41a by the supply pump 41, and in this process, $CO_2$ gas supplied to the water supply pipe 41a may be naturally introduced into the mixing hose 48 together with water.

In this case, the internal pressure of the mixing hose 48 may be changed by the water pressure of the supply pump 41, which can be verified using the pressure gauge 45.

$CO_2$ gas may be saturated in water by pressure due to introduction into the mixing hose 48, and $CO_2$ micro bubbles may be generated in water because the flow speed is changed when water passes the mixing hose 48. Also, while water passes through the filter member (not shown) disposed at the end portion of the mixing hose 48, micro bubble water containing micro bubbles of micrometer sizes may be generated.

Generated micro bubble water may be sent to the floatation separator 20 for floatation-separating and concentrating micro algae that are partially precipitated and discharged, and other micro algae may be supplied to and mixed with recycled culture medium to be sent the photo-bioreactor (first photo-bioreactor) 10 for culturing micro algae.

The systems according to the embodiments of the present invention have the following advantageous effects, for example. They do not require a separate compressor and a diffuser for supplying $CO_2$ gas to the photo-bioreactor unit 10, thereby lowering operation cost. They do not require a huge space for operation. They can treat $CO_2$ gas more efficiently, simply, and cost-effectively.

The invention has been described in detail with reference to exemplary embodiments thereof. However, it will be appreciated by those skilled in the art that changes may be made in these embodiments without departing from the principles and spirit of the invention, the scope of which is defined in the appended claims and their equivalents.

What is claimed is:

1. A system for culturing and recovering micro algae, comprising;
    a photo-bioreactor unit for culturing micro algae by a photochemical reaction to produce a micro algae precipitate;
    a floatation separator for separating the precipitated micro algae;
    a centrifugal separator for concentrating the separated micro algae;
    a micro bubble generator for generating process water containing micro carbon dioxide bubbles and supplying the generated process water to the photo-bioreactor unit and the floatation separator; and
    a culture medium regenerator for receiving waste culture medium from at least one of the photo-bioreactor unit, the floatation separator, and the centrifugal separator and regenerating the receive waste culture medium by supplementing nutrients;
    wherein the photo-bioreactor unit comprises a photo-bioreactor including: a culture vessel for containing therein culture medium and micro algae; and an overflow pipe longitudinally inserted into the culture vessel such that one end of the overflow pipe is positioned inside culture vessel and the other end of the overflow pipe is positioned outside the culture vessel,
    wherein the culture vessel includes: an inlet for receiving the regenerated culture medium from the culture medium regenerator, the water containing micro carbon dioxide bubbles from the micro bubble generator, or both: and an outlet for discharging the culture medium, micro algae, or both contained in the culture vessel,
    wherein the photo-bioreactor is equipped with a micro algae discharger for discharging micro algae precipitated at a lower portion of the culture vessel, the micro algae discharger comprising; a hopper for holding therein precipitated micro algae; a precipitation algae transfer pipe connected to a lower end the hopper; a sensor for measuring the height of the precipitated micro algae in the hopper; an upper separation plate provided between the culture vessel and the hopper and configured to be folded such that the culture vessel and the hopper are in communication with each other, if the height of the precipitated micro algae is less than a predetermined value and to be unfolded such that the culture vessel and the hopper are not in communication with each other, if the height of the precipitated micro algae is the same as or greater than the predetermined value; a lower separation plate provided between the hopper and the precipitation algae transfer pipe and configured to be unfolded such that the hopper and the precipitation algae transfer pipe are not in communication with each other, if the height of the precipitated micro algae is less than the predetermined value and to be folded such that the hopper and the precipitation algae transfer pipe are in communication with each other, if the height of the precipitated micro algae is the same as or greater than the predetermined value; and a separation plate controller for receiving a signal from the sensor and driving the upper and lower separation plates, respectively.

2. The system of claim 1, wherein the regenerated culture medium is supplied to the photo-bioreactor unit by a circulation pump.

3. The system of claim 1, wherein the floatation separator comprises:
    a floatation tank for receiving the process water from the micro bubble generator and the micro algae from the precipitation algae transfer pipe and mixing them;
    a floatation plate disposed in the floatation tank for inducing the micro algae to be floated;
    a skimmer disposed at an upper portion of the floatation tank for removing the floated micro algae;
    a micro algae storage tank for storing the micro algae removed by the skimmer; and
    a waste culture medium storage tank for storing waste culture medium after the removal of micro algae.

4. The system of claim 3, wherein the floatation separator further comprises a micro bubble floatation plate for inducing micro carbon dioxide bubbles contained in the process water to be floated.

5. The system of claim 1, wherein the floatation separator further comprises a micro bubble floatation plate for inducing micro carbon dioxide bubbles contained in the process water to be floated.

6. The system of claim 1, wherein the micro bubble generator comprises:
    a supply pump for supplying water to a supply pipe;
    a storage tank for storing carbon dioxide gas;
    a supply nozzle for supplying the carbon dioxide gas stored in the storage tank to the supply pipe; and
    a mixing chamber for receiving and mixing the water and the carbon dioxide gas supplied through the supply pipe to produce the processing water containing micro carbon dioxide bubbles.

7. The system of claim 6, wherein the mixing chamber comprises:
    an inlet for receiving the water and the carbon dioxide gas supplied through the supply pipe;
    an outlet for discharging the processing water containing micro carbon dioxide bubbles; and
    a mixing hose having one end connected to the inlet of the mixing chamber and the other end connected to the outlet of the mixing chamber, and configured to micronize the carbon dioxide gas supplied with the water into micro bubbles to produce the processing water containing micro carbon dioxide bubbles.

8. The system of claim 7, wherein the mixing chamber further comprises a support disposed therein around which the mixing hose is spirally wound.

9. The system of claim 1, wherein the photo-bioreactor unit comprises a plurality of the photo-bioreactors in series such that culture medium discharged from an outlet of one photo-bioreactor is introduced an inlet of another photo-bioreactor.

* * * * *